US006280436B1

(12) United States Patent
Freeman et al.

(10) Patent No.: US 6,280,436 B1
(45) Date of Patent: Aug. 28, 2001

(54) EYE TRACKING AND POSITIONING SYSTEM FOR A REFRACTIVE LASER SYSTEM

(75) Inventors: Jerre M. Freeman; James F. Freeman, both of Memphis; Roy E. Williams, Collierville, all of TN (US)

(73) Assignee: Memphis Eye & Cataract Associates Ambulatory Surgery Center, Memphis, TN (US)

( * ) Notice: Subject to any disclaimer, the term of this patent is extended or adjusted under 35 U.S.C. 154(b) by 0 days.

(21) Appl. No.: 09/371,195

(22) Filed: Aug. 10, 1999

(51) Int. Cl.$^7$ .................................................. A61B 18/18
(52) U.S. Cl. .............................. 606/5; 606/4; 606/10; 606/11; 606/12; 606/13; 607/89; 128/898
(58) Field of Search ............................. 606/4–6, 10, 11, 606/12, 13, 17, 41; 351/200, 237; 128/898

(56) References Cited

U.S. PATENT DOCUMENTS

| 3,839,641 | * | 10/1974 | Cooke et al. .......................... 250/369 |
| 4,230,129 | * | 10/1980 | LeVeen ................................. 128/804 |
| 4,771,785 | | 9/1988 | Duer ..................................... 128/653 |
| 4,848,340 | | 7/1989 | Bille et al. .......................... 128/303.1 |
| 4,870,964 | * | 10/1989 | Bailey, Jr. et al. ................ 128/303.1 |
| 5,098,426 | * | 3/1992 | Sklar et al. ................................ 606/5 |
| 5,398,356 | | 3/1995 | Pfleger ...................................... 5/608 |
| 5,597,146 | | 1/1997 | Putman ............................... 248/276.1 |
| 5,615,430 | | 4/1997 | Nambu et al. ............................ 5/600 |
| 5,634,920 | * | 6/1997 | Hohla ..................................... 606/12 |
| 5,748,366 | | 5/1998 | Yasunaga et al. .................... 359/368 |
| 5,769,787 | * | 6/1998 | Lemelson .............................. 600/407 |
| 5,865,832 | * | 2/1999 | Knopp et al. .......................... 606/10 |
| 5,899,857 | * | 5/1999 | Wilk ...................................... 600/407 |
| 5,928,221 | * | 7/1999 | Sasnett et al. ............................. 606/5 |
| 5,931,832 | * | 8/1999 | Jensen ...................................... 606/1 |
| 5,947,955 | * | 9/1999 | Kadambi et al. ......................... 606/4 |
| 5,980,513 | * | 11/1999 | Frey et al. .............................. 606/10 |
| 5,982,555 | * | 11/1999 | Melville et al. ....................... 359/630 |
| 5,984,916 | * | 11/1999 | Lia ........................................ 606/11 |
| 6,030,376 | * | 2/2000 | Arashima et al. ........................ 606/4 |
| 6,045,227 | * | 4/2000 | Stewart et al. ........................ 351/237 |
| 6,099,522 | * | 8/2000 | Knopp et al. .......................... 606/10 |
| 6,139,542 | * | 10/2000 | Hohla ...................................... 606/5 |
| 6,146,375 | * | 11/2000 | Juhasz et al. ............................. 606/6 |
| 6,149,643 | * | 11/2000 | Herekar et al. .......................... 606/5 |
| 6,152,599 | * | 11/2000 | Salter, Jr. ............................. 378/209 |
| 6,159,202 | * | 12/2000 | Sumiya et al. ........................... 606/4 |

FOREIGN PATENT DOCUMENTS

WO 97/46184 * 11/1997 (WO) ............................... A61F/9/01

* cited by examiner

*Primary Examiner*—Linda C. M. Dvorak
*Assistant Examiner*—Ahmed Farah
(74) *Attorney, Agent, or Firm*—David P Gordon; Davis S Jacobson; Thomas A Gallagher

(57) ABSTRACT

An eye tracking and positioning system for use with a refractive laser system includes a camera interface, a computer, and a system for moving the patient relative to the laser beam. The computer includes a video frame grabber which extracts images of the eye from the camera, and is programmed to perform an eye tracking algorithm. The eye tracking algorithm calculates the exact center of the eye pupil, and compares the center with the desired location of the laser beam, as determined by a surgeon, with an image processing algorithm. If the relative location of the eye center and the laser beam fall outside a predetermined value, the patient chair, and thereby the patient, is repositioned relative to the laser beam, as opposed to the laser beam being repositioned relative to the patient. The repositioning counters the movement of the eye.

21 Claims, 4 Drawing Sheets

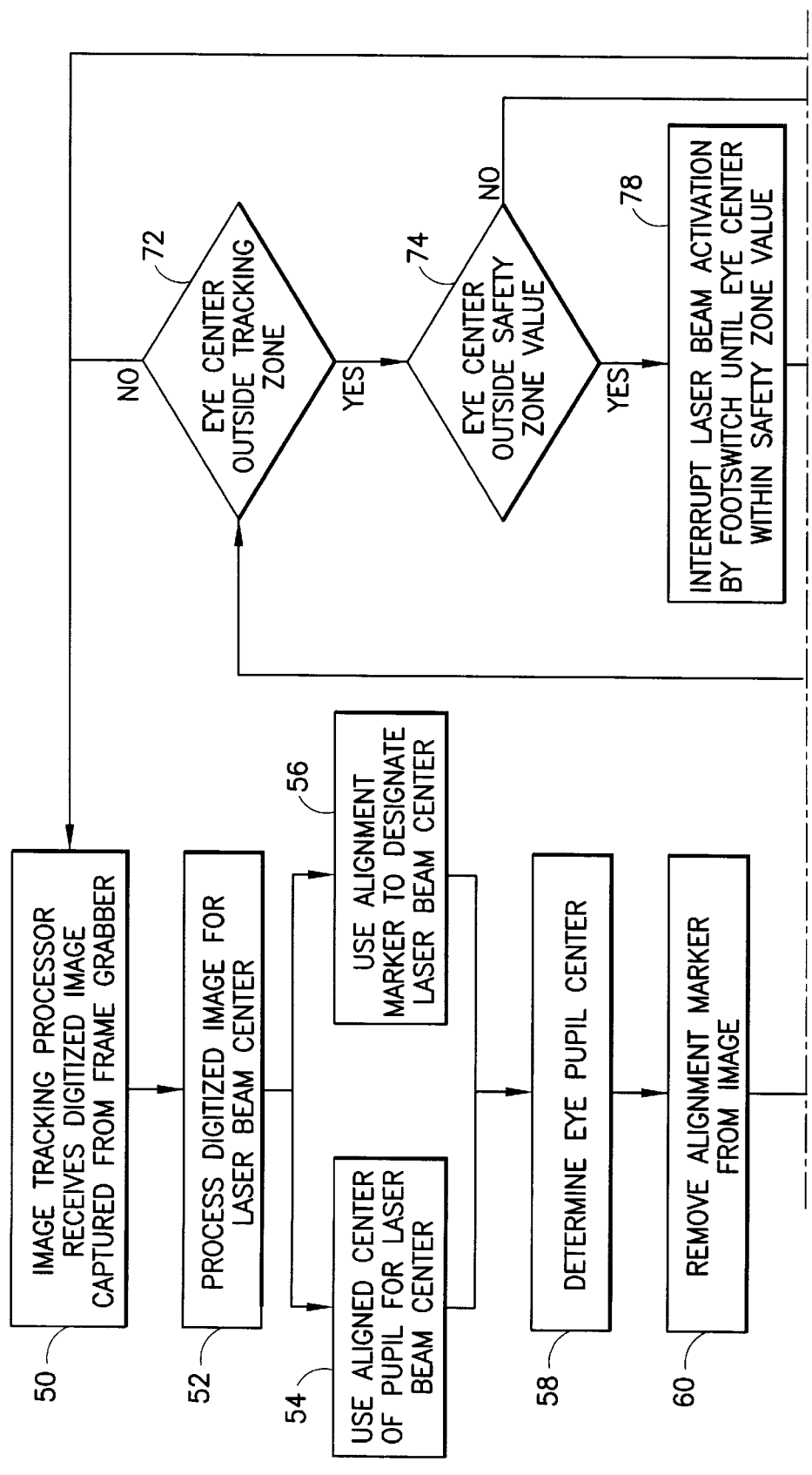

EYE TRACKING AND POSITIONING SYSTEM FOR A REFRACTIVE LASER SYSTEM

BACKGROUND OF THE INVENTION

1. Field of the Invention

This invention relates broadly to eye surgery. More particularly, this invention relates to refractive laser systems for eye surgery.

2. State of the Art

The excimer laser refractive surgery field has exploded over the past few years with many new lasers systems to correct human vision. These systems use an ultraviolet excimer laser to change the shape of the cornea in a calculated pattern which makes it possible for the eye to focus properly. For example, in the treatment of myopia, the laser is used to remove tissue from the cornea in order to flatten its shape. The correction of hyperopia is produced by steepening the cornea. The correction of astigmatism requires the laser to remove tissue in a more complex pattern. All of these procedures require precise shaping of the cornea which depends on accurate placement of the laser beam. Therefore, any eye movement can affect the placement of the laser beam.

Most currently approved broadbeam refractive laser systems and scanning spot systems do not incorporate eye tracking. Therefore, the patient is required to minimize eye movement during surgery by voluntarily fixating their eyes on a small light located just above the patient. When the average person fixates on something, he or she has about five saccadic eye movements per second. Saccadic eye movements are rapid, involuntary movements that are random in amplitude and direction. These movements can cause eccentricity of the laser beam, resulting in degraded laser vision correction predictability and visual quality.

Newer generation refractive laser systems that use small scanning spots, usually less than 1 mm in diameter, have implemented eye-tracking techniques that move the laser beam to adjust for eye movement. Early indications suggest that this approach provides a higher accuracy ablation by virtually eliminating shaping error caused by eye movement.

Nevertheless, there already exists a large number of broadbeam and scanning spot systems which are not provided with eye tracking capability. There is currently no available means by which to provide existing systems with eye tracking capability.

SUMMARY OF THE INVENTION

It is therefore an object of the invention to provide an eye tracking and positioning system for a refractive laser system which compensates for eye movement in a manner different than prior art eye tracking devices.

It is another object of the invention to provide an eye tracking and positioning system which is capable of being retrofit to existing broadband and scanning spot refractive laser systems without modifying any hardware in the laser system.

It is another object of the invention to provide a refractive laser system which is adapted to move the patient, and thus the eye of the patient, relative to the laser beam.

In accord with these objects, which will be discussed in detail below, an eye tracking and positioning system is provided for use with a refractive laser system which produces a laser for surgically reshaping the eye. The eye tracking and positioning system includes a means for capturing images of the eye, a computer, and a means for moving the patient relative to the laser beam. The computer preferably includes a video frame grabber which captures images from a camera of the laser system, and is programmed to perform an eye tracking algorithm with respect to the images. The eye tracking algorithm calculates the exact center of the eye pupil in the image, and compares the center with the desired location of the laser beam, as determined by a surgeon, with an image processing algorithm. If the relative location of the eye center and the laser beam fall outside a predetermined value, the means for moving the patient relative to the laser beam are activated. The means for moving the patient is preferably a surgical bed, surgical chair, or headrest which is motorized to move the patient relative to the laser beam (as opposed to moving the laser beam relative to the patient) to make the necessary adjustment to the current position of the eye and thereby counter the movement of the eye.

The eye tracking and positioning system of the invention may be retrofit to the existing broadbeam and scanning spot systems which do not already include eye tracking capability. Additionally, the eye tracking and positioning system may be provided as an integral part of new refractive laser surgery systems.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
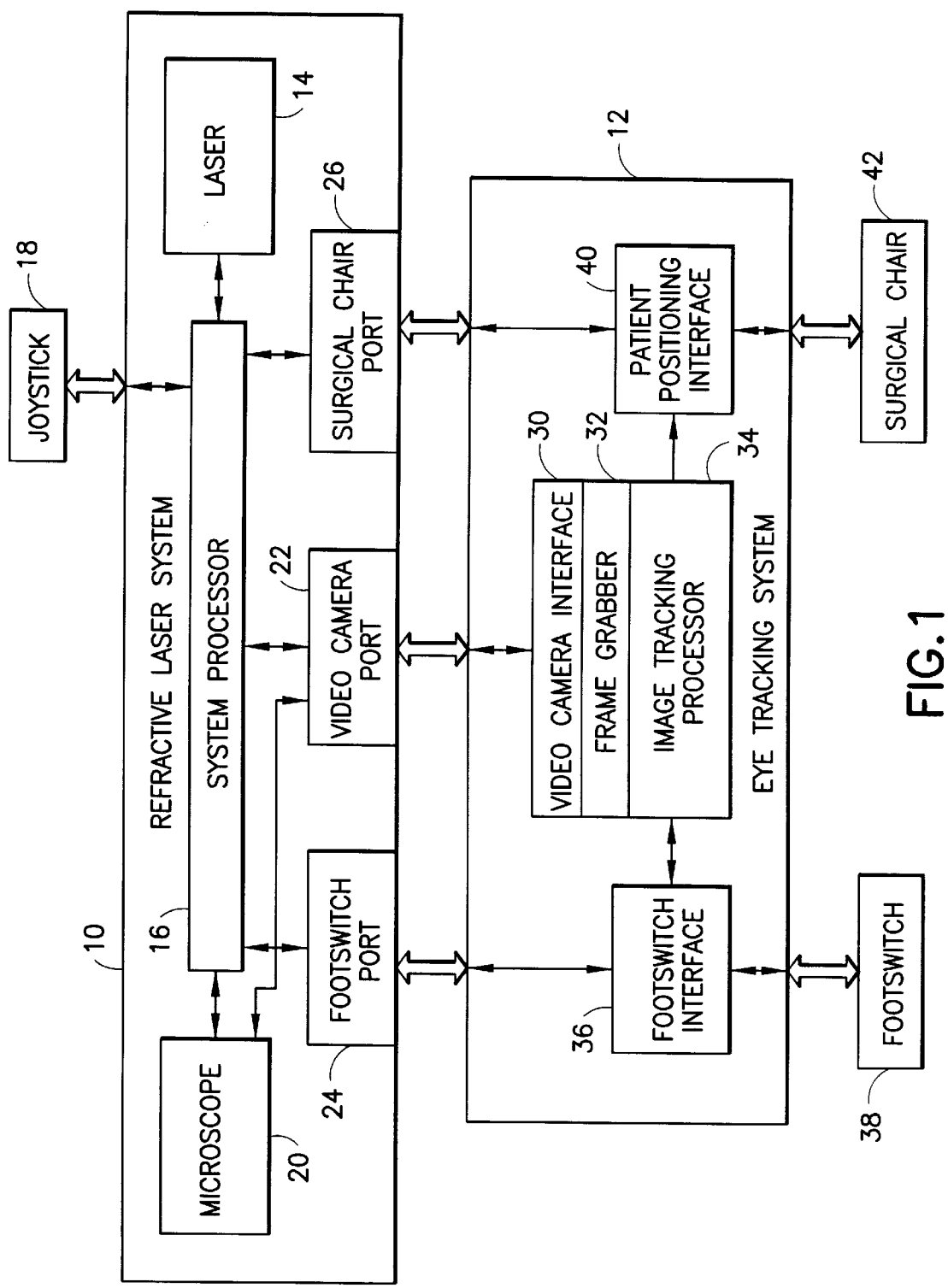
FIG. 1 is a schematic view of a refractive laser system provided with the eye tracking and positioning system of the invention.

Turning now to FIG. 1, a refractive laser system 10 is coupled to an eye tracking computer system 12 of the invention. The refractive laser system 10 includes a laser 14 coupled to a system processor 16, a joystick 18 coupled to the system processor 16 for positioning a surgical chair 42, and a surgical microscope 20 for viewing an eye of a patient seated in the surgical chair 42. The refractive laser system 10 also includes a video-out camera port 22 coupled to the microscope, and a footswitch port 24 and a surgical chair port 26.

The eye tracking computer system 12 generally includes a video camera interface 30 which is coupled to the video-out port 22, a frame grabber 32, and an image tracking processor 34, preferably implementing a software algorithm described below. The computer system 12 also includes a footswitch interface 36 and a patient positioning interface 40. The footswitch interface 36 is coupled between the footswitch port 24 and a footswitch 38. When the footswitch 38 is activated, the laser 14 is activated to emit a laser beam, as described in more detail below. The computer 12 also includes a patient positioning interface 40 which is coupled between the surgical chair port 26 and the surgical chair (or bed or headrest) 42. The surgical chair 42 is provided with motors capable of relatively rapidly repositioning the chair such that an eye of a patient in the chair is moved relative to a laser beam emitted by the laser 14.

More particularly, the video-out camera port 22 to which the video camera interface 30 is coupled is typically a microscope beam splitter optical port which permits users to attach cameras thereto for recording the surgery and audience viewing of the surgery. The eye tracking system 12 takes advantage of one of these microscope beam splitter optical ports in order to monitor the eye via a provided video camera. For example, in the VISX™ laser, an electronic output signal port connector is provided which is attached to an internal CCD camera. On other systems an electronic signal splitter can be attached at the output of the camera so the signal may be captured by the video camera interface 30. Alternatively, a separate camera (not shown) may be provided with the eye tracking system of the invention and added to the microscope beam splitter optical port in order to capture the images. That is, any number of methods and systems may be utilized to capture the image of the eye from the surgical microscope 20 used in performing the refractive laser surgery.

The frame grabber 32, e.g., a National Instruments PCI 1408, takes the signal from the video camera interface 30 and converts it to a digital signal, preferably in real-time. The frame grabber 32 can be configured to capture color, monochrome or infrared images at varying speeds. The digitized signal is then converted to a digital image matrix for processing. This conversion occurs at the rate of the camera (from a typical 30 Hz for color cameras to as fast as 800-Hz for monochrome cameras).

The image tracking processor 34 receives the digitized image from the frame grabber 32 and generally (1) processes the digitized image for laser beam center, (2) processes the digitized image for pupil recognition, (3) determines the center of the pupil, and (4) calculates the offset of the current eye pupil center from a surgeon-desired offset and drives the appropriate surgical chair motors. Each of the functions of the image tracking processor 34 are preferably performed by an algorithm carried out by the image tracking processor 34, and will now be described in more detail.

Figure 2B:
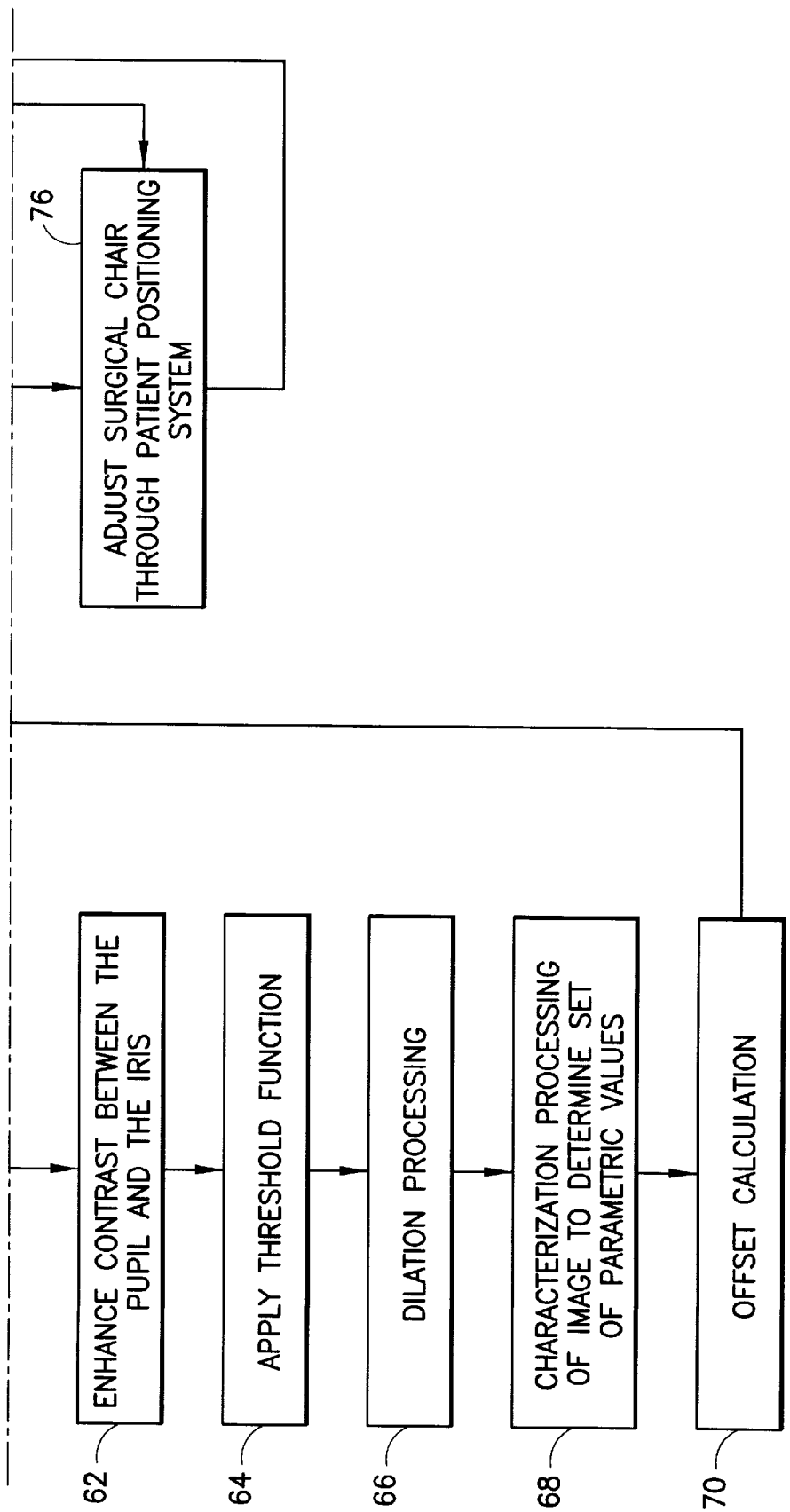
FIG. 2 is a flow chart of the process of the invention.

Referring to FIGS. 1 and 2, when the surgeon presses the footswitch 38, the current image in the camera is digitally captured at 50 by the frame grabber 32 for processing. The digitized image is processed at 52 to determine a laser beam center (reference location) preferably by one of two methods. Both methods begin by monitoring the footswitch 38 during continuous acquisition of the eye image signal entering from the video camera interface 30.

According to a first method 54, the center of the pupil is used as the laser beam center. That is, the surgeon positions the eye with respect to an alignment marker (e.g., a reticle appearing in the microscope 20 or displayed on a video monitor). Positioning is performed by adjustment of the surgical chair 42 via movement of the joystick 18. Once the eye is properly positioned, the surgeon presses the footswitch 38 and the image tracking processor 34 uses the current eye pupil center as the laser beam center. The image tracking processor 34 then continues to the next step of actively tracking the eye pupil center and directing the surgical chair motors so that the laser beam and eye are properly relatively positioned.

According to a second method at 56, the surgeon or a surgical technician uses a laser system alignment marker (e.g., a reticle or a visible laser diode spot) to designate the laser beam center. This second method permits the laser beam to be centered away from the pupil center. When the surgeon has the eye at a desired location, the surgeon presses the footswitch 38 and the image tracking processor 34 captures the current image. For surgeon positioning, this image is preferably then processed to highlight the alignment marker, which appears brighter than the pupil in a monochrome image, or appears as a different color than the pupil in a color image. The alignment marker is determined and its center is found and recorded as the desired laser beam center. For surgical technician positioning, preferably a PC mouse cursor is used by the technician to mark the position of the reticle or the alignment spot. The coordinates of the mouse cursor are recorded as the desired laser beam center. The image tracking processor 34 then continues to the next step of actively tracking the eye pupil center and directing the surgical chair motors.

Regardless of whether the first or second methods are used for determining the laser beam center, the image tracking processor next determines at 58 the eye pupil center. That is, once the desired laser beam reference location is determined at 54 or 56, the image tracking processor 34 begins to track the eye pupil center. There are several image processing methods that can be used to find the pupil and pupil center. One preferred method implemented by the image tracking processor 34 uses the contrast between the pupil and the iris to determine the pupil and then the center of the pupil by the following seven steps.

First, the alignment marker is removed at 60 from the image. Although the alignment marker is useful to help determine the desired laser center beam, it does interfere with detection of the pupil. As the alignment marker appears white against the darker pupil, alignment marker removal from a monochrome image is preferably performed with a high order low pass filter. In a color image, the marker is removed by ignoring the color plane that corresponds to its color (usually red).

Second, at 62, the contrast between the pupil and the iris is enhanced. This is preferably done by applying a transfer function to the intensity values in the image to produce a bimodal histogram of intensity values. The transfer function increases the brightness and contrast in dark regions (the pupil) and decreases the contrast in brighter regions (iris). The intensity values are preferably then reversed to produce a photometric negative of the image. Preferably, the photometric image is used in the image processing steps which follow.

Third, a threshold function is applied to the photometric image at 64 to create a binary representation of the image which permits faster image processing. The threshold function replaces the image intensity values below some threshold value to black (a value of zero) while placing the intensity values above the threshold value to all white (a value of 256 in an 8-bit image representation); i.e., a binary representation of the image is created. At this step the image of the pupil is now totally white against a black background.

Fourth, the binary representation is preferably further processed at 66 by a technique known as dilation. Dilation ensures that the pupil is a solid circular object. This step is preferred as sometimes the alignment marker, especially the reticle, will leave black holes or lines in the pupil area.

Fifth, at 68, the binary image undergoes a characterization process to determine a set of parametric values from the image. Since all pupils are nearly the same diameter (for recognition purposes), the search of binary objects can be limited to a range defined by pupil diameters. This range is typically 2–3 millimeters. A search is then performed on the binary image for objects matching the criterion. Those objects found in this range are returned with several pieces of information. By limiting the field-of-view to the eye image, only one object, the pupil, will be detected. The information returned from this function include object area, width and height, and object center. The object center is used for the pupil center. The object width and height are used to apply a bounding circle around the displayed pupil during the tracking procedure.

Sixth, an offset calculation is made at 70 in which the object (pupil) center is compared against the previously defined laser beam center and differences are recorded. If, at 72, the difference is less than or equal to a surgeon preset value, i.e., a predetermined tracking zone, the surgical chair is not adjusted, the laser is permitted to operate, and the image tracking system 34 continues to receive, at 50, and process, at 52, 54 (or 56), 58, 60, 62, 64, 66, 68 and 70, images of the eye.

Seventh, if the eye center value falls outside the surgeon preset value, at 72, the patient, and consequently the eye, is repositioned at 76 by adjusting the surgical chair 42 in the proper direction, as described below.

Furthermore, if the eye center falls outside the surgeon preset value at 72 and also a predetermined safety zone (a second predetermined value greater than the predetermined tracking zone) at 74, the image tracking processor 34 sends a command to interrupt one stage (FS1 in FIG. 3) of the footswitch 38, thus pausing the laser surgery procedure, and also repositions the patient at 76 by adjusting the surgical chair 42 in the proper direction, as described below. Then, once repositioned, the laser is again permitted to operate (i.e., the footswitch is reset), and, at 50, the image tracking system 34 continues to receives and process images of the eye.

Figure 3:
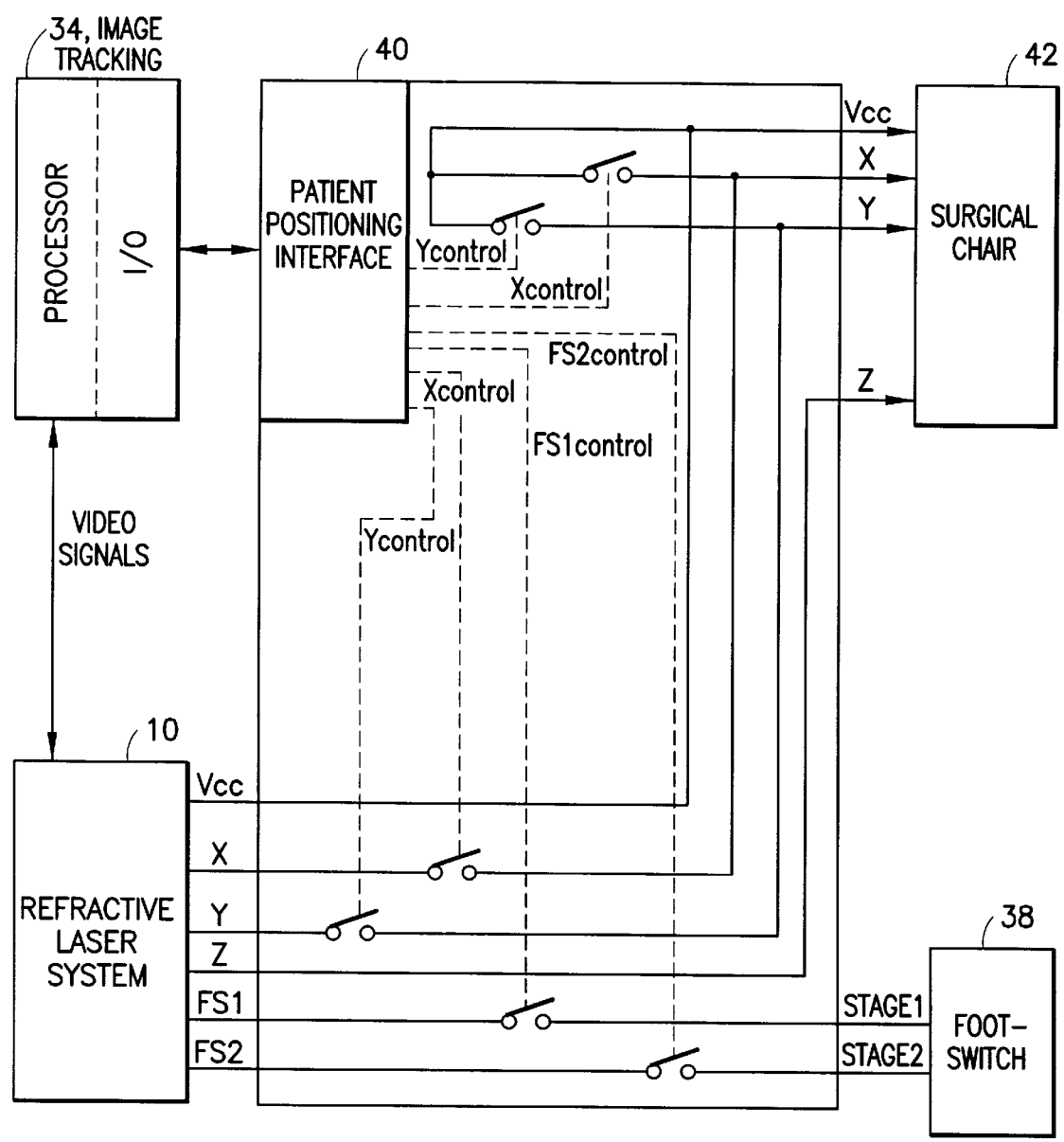
FIG. 3 is a schematic view of the patient positioning interface of the invention.

Referring to FIGS. 1 and 3, if a command is sent to adjust the surgical chair at 76, the patient positioning interface 40 performs two functions: (1) adjustment of the chair 42 and patient to counter the eye motion and, if the eye center is outside the safety zone at 74, (2) interruption at 78 of the signal from the footswitch 38, as a safety measure. Each of these functions will now be described in more detail.

First, turning to FIG. 3, an adjustment signal determined by the image tracking processor 34 is sent at 76 to the patient positioning interface 40 for adjustment of the surgical chair 42. The patient positioning interface 40 provides the appropriate signal to direct the chair motors. For example, one model of a Dexta™ surgical chair, well-known in the field of eye refractive surgery, utilizes relays to provide fixed voltages to positioning motors in the chair. In the Dexta™ surgical chair, four relays provide +X, −X, +Y, and −Y directional movement. Z directional control voltages may also be used. According to a preferred patient positioning interface 40, the relays are turned OFF or ON depending on the tracking adjustment required. Additionally or alternatively, variable control voltages may be supplied to the chair controller. These voltages then control silicon controlled rectifier (SCR) drives to control the motors moving the chair. This allows for finer motion control of the patient. The patient positioning interface 40 provides these variable voltages to the appropriate motors to adjust the eye position of the patient. Other beds or chairs used in this field have similar controls and may likewise be coupled to the patient positioning interface 40. In addition, the invention may be used with a headrest which includes motor control to appropriately adjust the eye position of the patient.

Second, interruption at 78 of a stage of the footswitch 38 (i.e., interruption of the footswitch signal FS1 in FIG. 3) pauses the laser procedure when the eye drifts outside the safety zone at 74. That FS1 stage of the footswitch is re-enabled once the eye is returned to the safety zone by adjustment of the surgical chair.

There have been described and illustrated herein several embodiments of an eye tracking and positioning system for a refractive laser system and a method of tracking an eye and repositioning the eye relative to a laser beam. While particular embodiments of the invention have been described, it is not intended that the invention be limited thereto, as it is intended that the invention be as broad in scope as the art will allow and that the specification be read likewise. Thus, while particular functional systems have been disclosed, it will be appreciated that other functional systems may be used as well. That is, the image tracking processor and patient positioning interface may be combined in a single system or further divided to perform the required tasks of the invention. Furthermore, while a particular preferred method has been disclosed for tracking the pupil of the eye, it will be appreciated that other algorithms may be used. For example, the eye center can be determined from a marker in a manner other than described above. In one implementation, an active infrared diode system places one or more small, collimated spots on the cornea, and an infrared detector system is then used to monitor the one or more spots. For example, three spots can be monitored to triangulate the center of the eye during eye movement. It will therefore be appreciated by those skilled in the art that yet other modifications could be made to the provided invention without deviating from its spirit and scope as so claimed.

What is claimed is:

1. An eye tracking and positioning system for use with a refractive laser system which produces a laser beam for performing surgery on an eye of a patient, the refractive laser system having a video-out port, said eye tracking and positioning system comprising:
   a) a computer system including,
      i) a means for receiving an image of the eye from the video-out port,
      ii) a means for processing the image, and
      iii) a means determining from the processed image whether the eye is properly positioned relative to the laser beam; and
   b) adjustment means for adjustably moving the patient relative to the laser beam based on input to said adjustment means from said computer system.

2. An eye tracking and positioning system according to claim 1, wherein:
   said adjustment means is adapted to move the patient in X and Y directions, such that when said computer system determines that the eye is mispositioned relative to the laser beam, said adjustment means moves the patient to result in proper relative positioning of the eye of the patient and the laser beam.

3. An eye tracking and positioning system according to claim 1, wherein:
   said image is a digital image.

4. An eye tracking and positioning system according to claim 3, wherein:
   said means for receiving an image from the video-out port is a digital frame grabber.

5. An eye tracking and positioning system according to claim 1, wherein:
   said means for processing the image includes a processor means for,
      A) processing the image for eye pupil recognition,
      B) determining a center of the eye pupil, and C) calculating an offset of the center of the eye pupil from a laser beam reference location.

6. An eye tracking and positioning system according to claim 5, wherein:

said processor means is further for determining whether the offset is greater than a predetermined value.

7. An eye tracking and positioning system according to claim 6, wherein:

said computer system includes means for sending a signal, wherein when said offset is greater than said predetermined value, means for sending a signal sends a signal to said adjustment means.

8. An eye tracking and positioning system according to claim 5, wherein:

said processor means determines the center of the eye pupil by increasing the contrast between the pupil and an iris surrounding the pupil in said image.

9. An eye tracking and positioning system according to claim 8, wherein:

said image is a digital image including a plurality of intensity values, and the contrast is increased by said processor means applying a transfer function to the intensity values in the digital image to produce a bimodal histogram of the intensity values.

10. An eye tracking and positioning system according to claim 9, wherein:

said processor means determines the center of the eye pupil by further applying a threshold function to the bimodal histogram to create a binary representation of the image.

11. An eye tracking and positioning system according to claim 10, wherein:

said processor means processes said binary representation to ensure that the pupil is a circular object.

12. An eye tracking and positioning system according to claim 10, wherein:

said processor means searches said binary representation for objects having a size approximately the size of a human pupil.

13. An eye tracking and positioning system according to claim 5, wherein:

said processor means is further for determining the laser beam reference location.

14. An eye tracking and positioning system according to claim 13, wherein:

said processor means assigns the center of the pupil as the laser beam reference location.

15. An eye tracking and positioning system according to claim 13, wherein:

said processor means sets a laser beam reference location in alignment with an alignment marker.

16. An eye tracking and positioning system according to claim 1, wherein:

said adjustment means is one of a motorized surgical chair and a motorized surgical bed.

17. An eye tracking and positioning system according to claim 1, wherein:

said adjustment means is a motorized patient headrest.

18. An eye tracking and positioning system according to claim 1, further comprising:

c) a switch which activates said means for receiving a digital image of the eye from the video-out port.

19. An eye tracking and positioning system according to claim 1, further comprising:

c) a laser system which produces a laser beam for performing surgery on the eye of the patient.

20. An eye tracking and positioning system according to claim 19, further comprising:

d) a microscope which provides a magnified image of the eye and has means for supplying a video signal to the video-out port.

21. A method for positioning an eye of a patient relative to a laser beam produced by a refractive laser system for performing eye surgery on the eye, the method including:

a) obtaining an image of the eye;

b) processing the image;

c) determining from the processed image whether the eye is properly positioned relative to the laser beam; and then d) if the eye is not properly positioned relative to the laser beam, moving the patient relative to the laser beam to properly position the eye relative to the laser beam.

* * * * *

UNITED STATES PATENT AND TRADEMARK OFFICE
CERTIFICATE OF CORRECTION

PATENT NO.    : 6,280,436 B1
DATED         : August 28, 2001
INVENTOR(S)   : Jerre M. Freeman et al.

It is certified that error appears in the above-identified patent and that said Letters Patent is hereby corrected as shown below:

<u>Column 8,</u>
Line 41, before the word "moving", insert -- automatically --.

Signed and Sealed this

Sixth Day of August, 2002

Attest:

JAMES E. ROGAN
Attesting Officer        Director of the United States Patent and Trademark Office